US011873340B2

(12) United States Patent
Dekaban et al.

(10) Patent No.: US 11,873,340 B2
(45) Date of Patent: Jan. 16, 2024

(54) ANTI-CD11D ANTIBODIES AND USES THEREOF

(71) Applicants: The University of Western Ontario, London (CA); ELI LILLY AND COMPANY, Indianapolis, IN (US)

(72) Inventors: Gregory Dekaban, London (CA); Arthur Brown, London (CA); Lynne Weaver, London (CA); Allan Barrett, Indianapolis, IN (US); Kristine Kikly, Indianapolis, IN (US)

(73) Assignees: The University of Western Ontario, London (CA); Eli Lilly and Company, Indianapolis, IN (US)

( * ) Notice: Subject to any disclaimer, the term of this patent is extended or adjusted under 35 U.S.C. 154(b) by 1543 days.

(21) Appl. No.: 16/078,813

(22) PCT Filed: Feb. 24, 2017

(86) PCT No.: PCT/CA2017/050240
§ 371 (c)(1),
(2) Date: Aug. 22, 2018

(87) PCT Pub. No.: WO2017/143451
PCT Pub. Date: Aug. 31, 2017

(65) Prior Publication Data
US 2023/0183355 A1 Jun. 15, 2023

Related U.S. Application Data
(60) Provisional application No. 62/300,160, filed on Feb. 26, 2016.

(51) Int. Cl.
C07K 16/28 (2006.01)
A61P 37/06 (2006.01)
A61P 25/00 (2006.01)
A61K 39/00 (2006.01)

(52) U.S. Cl.
CPC .......... C07K 16/2845 (2013.01); A61P 25/00 (2018.01); A61P 37/06 (2018.01); *A61K 2039/505* (2013.01); *C07K 2317/24* (2013.01); *C07K 2317/565* (2013.01); *C07K 2317/92* (2013.01)

(58) Field of Classification Search
CPC ............ C07K 16/2845; C07K 2317/24; C07K 2317/565; C07K 2317/92; A61K 2039/505
See application file for complete search history.

(56) References Cited

U.S. PATENT DOCUMENTS 6,620,915 B2  9/2003  Gallatin et al.
2007/0092515 A1  4/2007  Weaver et al.

FOREIGN PATENT DOCUMENTS

JP    2007510738       4/2007
WO    2000029446       5/2000
WO    WO-2006116002 A2 * 11/2006   .............. C07K 16/22
WO    WO-2016028672 A1 *  2/2016   ........... A61K 39/395

OTHER PUBLICATIONS

Bao F, Dekaban GA, Weaver LC. J Neurochem. Sep. 2005;94(5):1361-73. doi: 10.1111/j.1471-4159.2005.03280.x. Epub Jun. 30, 2005. PMID: 15992367. (Year: 2005).*
Gonzalez-Sapienza G, Rossotti MA, Tabares-da Rosa S. Front Immunol. Aug. 21, 2017;8:977. doi: 10.3389/fimmu.2017.00977. PMID: 28871254; PMCID: PMC5566570. (Year: 2017).*
Kussie PH, Parhami-Seren B, Wysocki LJ, Margolies MN. J Immunol. Jan. 1, 1994;152(1):146-52. PMID: 8254187. (Year: 1994).*
Chen C, Roberts VA, Stevens S, Brown M, Stenzel-Poore MP, Rittenberg Mb. EMBO J. Jun. 15, 1995;14(12):2784-94. doi: 10.1002/j.1460-2075.1995.tb07278.x. PMID: 7796805; PMCID: PMC398397. (Year: 1995).*
Remington, Joseph Price. Remington: The Science and Practice of Pharmacy. vol. 1. Lippincott Williams and Wilkins, 2006.
Bao, Feng, et al. "CD11d integrin blockade reduces the systemic inflammatory response syndrome after spinal cord injury." Experimental Neurology 231.2 (2011): 272-283.
Shultz, Sandy R., at al. "Treatment with an anti-CD11d integrin antibody reduces neuroinflammation and improves outcome in a rat model of repeated concussion." Journal of Neuroinflammation 10.1 (2013): 1-15.
Bao, Feng, et al. "A CD11d monoclonal antibody treatment reduces tissue injury and improves neurological outcome after fluid percussion brain injury in rats." Journal of Neurotrauma 29.14 (2012): 2375-2392.
Queen, Cary, et al. "A humanized antibody that binds to the interleukin 2 receptor." Proceedings of the National Academy of Sciences 86.24 (1989): 10029-10033.
PCT/CA2017/050240, Written Opinion of the ISA, dated May 8, 2017.
PCT/CA2017/050240, Int'l Search Report, dated May 17, 2017.
EP 17755688.3 Extended European Search Report, dated Oct. 2, 2019.
Bao et al. Experimental Neurology, Elsevier vol. 231, 2:272-283, Jul. 7, 2011.

* cited by examiner

Primary Examiner — Adam Weidner
Assistant Examiner — Laura Ann Essex
(74) Attorney, Agent, or Firm — Milstein Zhang & Wu LLC

(57) ABSTRACT

Antibodies to human CD11d, compositions comprising such CD11d antibodies, and methods of using such CD11d antibodies for the treatment of central nervous system trauma including spinal cord injury and traumatic brain injury, as well as systemic inflammatory response following central nervous system trauma.

18 Claims, 3 Drawing Sheets

Specification includes a Sequence Listing.

ANTI-CD11D ANTIBODIES AND USES THEREOF

STATEMENT REGARDING FEDERALLY SPONSORED RESEARCH OR DEVELOPMENT

This invention was made with government support under W81XWH-10-1-1014 & W81XWH-10-1-1018 awarded by US Army Department. The government has certain rights in the invention.

SEQUENCE LISTING

The instant application contains a Sequence Listing which has been filed electronically in ASCII format and is hereby incorporated by reference in its entirety. Said ASCII copy, created on Jun. 28, 2021, is named GWLG022US_SL.txt and is 17,998 bytes in size.

FIELD OF THE INVENTION

The present invention is in the field of medicine. Particularly, the present invention relates to antibodies to CD11d, compositions comprising such CD11d antibodies, and methods of using such CD11d antibodies for the treatment of central nervous system (CNS) trauma, including spinal cord injury (SCI) and traumatic brain injury (TBI), as well as systemic inflammatory response (SIRS) following CNS trauma.

BACKGROUND OF THE INVENTION

The $\beta_2$ integrin molecules are a class of transmembrane heterodimers comprising an $\alpha$ subunit in noncovalent association with a $\beta$ subunit. This membrane-associated class of molecules has been reported to actively participate in cellular adhesion. CD11d, also referred to as integrin subunit alpha-d ($\alpha_d$), is the a subunit of the heterodimeric $\beta_2$ integrin protein CD11d/CD18. CD11d has been reported as being expressed on a wide variety of immune cells including neutrophils, monocytes, macrophages, natural killer cells and some subsets of B and T cells, Although the expression, regulation, and distribution of CD11d is not fully understood, CD11d has been reported to play a role in immune and inflammatory responses.

Central nervous system (CNS) injuries are a diverse class of conditions (e.g., CNS trauma), including traumatic brain injury (TBI) and spinal cord injury (SCI), posing a major health problem worldwide. For example, it is estimated that each year approximately 1.7 million civilians in the United States alone sustain a TBI (U.S. Centers for Disease Control) and approximately 12,000 people sustain a SCI (National Spinal Cord Injury Statistical Center). A commonality among TBI and SCI is the debilitation that typically results, which is often severe and chronic. In both TBI and SCI, the initial trauma is often followed by inflammation that can cause considerable damage to surrounding tissue including neurons and glia. Current therapy options for both TBI and SCI include surgical intervention, physical and cognitive rehabilitation as well as analgesics, anti-convulsants and sedatives.

Systemic inflammatory response syndrome (SIRS) can also arise following traumatic CNS injury. SIRS is an inflammatory state affecting large regions of, and even, the entire body. SIRS is characterized by inflammatory cells from the circulation invading organs, potentially resulting in organ damage. Animal models have shown that, following TBI, release of brain-derived cytokines may initiate SIRS resulting in various secondary organ dysfunction impacting the neurological, psychological, cardiovascular, pulmonary and metabolic systems. Therapies for treating the symptoms of SIRS currently include antibiotics and steroids.

Antibodies to CD11d are known. For example, U.S. Pat. No. 6,620,915 and U.S. Patent publication number US 2007/0092515A1 disclose anti-CD11d antibodies and uses of such antibodies as potentially applicable in the treatment of a number of diseases including Type I diabetes, atherosclerosis, multiple sclerosis, asthma, psoriasis, lung inflammation, rheumatoid arthritis, acute respiratory distress, chronic pain, and CNS injury. However, to date no antibody targeting CD11d has been approved for therapeutic use, and the treatment options for patients suffering from CNS trauma remain limited and are an unmet need. Thus, there remains a need for alternative CD11d antibodies. In particular, there remains a need for alternative CD11d antibodies which specifically bind CD11d and which reduce the inflammatory response and improve neurological outcomes following CNS trauma.

SUMMARY OF THE INVENTION

Novel CD11d antibodies have now been developed that exhibit anti-inflammatory activity.

In one aspect of the invention, a CD11d antibody is provided that comprises a light chain variable region (LCVR) and a heavy chain variable region (HCVR), wherein the LCVR comprises the complementarity determining regions (CDRs) LCDR1, LCDR2 and LCDR3 and the HCVR comprises CDRs HCDR1, HCDR2 and HCDR3, wherein the amino acid sequence of LCDR1 is given by SEQ ID NO: 13, the amino acid sequence of LCDR2 is given by SEQ ID NO: 14, the amino acid sequence of LCDR3 is given by SEQ ID NO: 15, the amino acid sequence of HCDR1 is given by SEQ ID NO: 16, the amino acid sequence of HCDR2 is given by SEQ ID NO: 17, and the amino acid sequence of HCDR3 is given by SEQ ID NO: 18.

In another aspect, a humanized antibody is provided which exhibits a binding affinity for rat CD11d in the range of about 0.05 to 5.0 nm, and is capable of binding to human CD11d.

These and other aspects of the invention are described herein by reference to the following figures.

DESCRIPTION OF THE INVENTION

Figure 1:
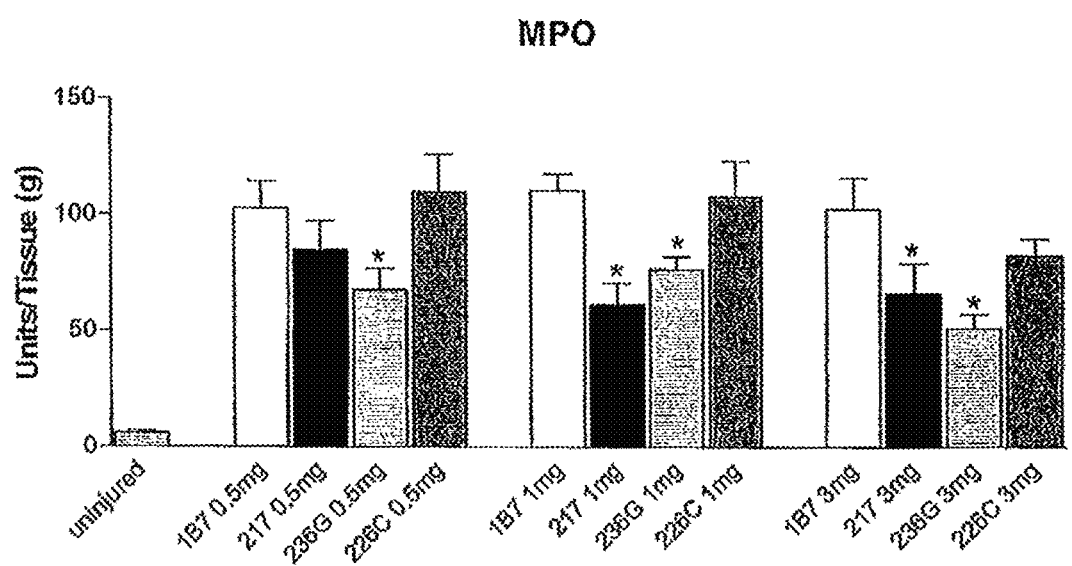
FIG. 1 graphically illustrates that, following experimentally induced SCI, rats treated with doses (0.5 mg/kg to 3.0 mg/kg) of either mouse mAb 217L or 236G demonstrate reduced MPO levels in protein homogenates from their lesion epicenters at 24 hr post-SCI (one-way ANOVA, $p<0.05$).
Figure 2:
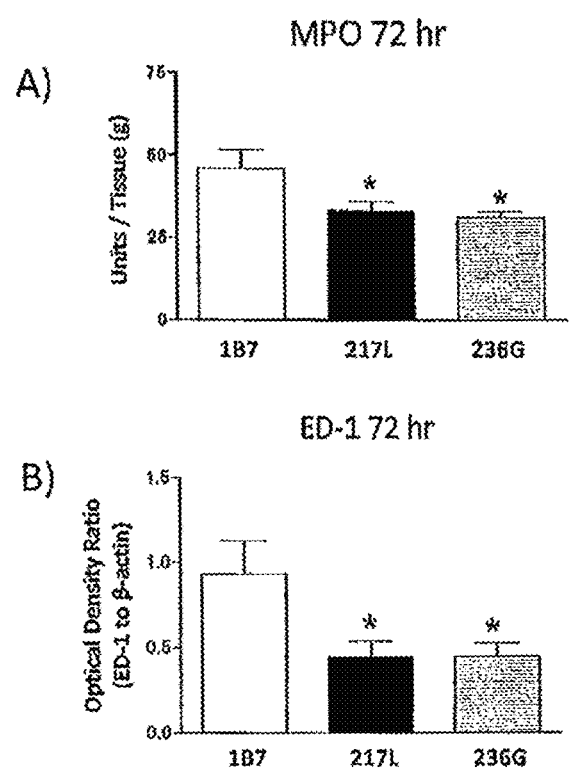
FIG. 2 graphically illustrates that, at 72 hr post-SCI, rats treated with mouse mAb 217L and 236G demonstrate reduced MPO activity and ED-1 levels in protein homogenates from their lesion epicenters (one-way ANOVA, $p<0.05$).

The present invention provides an antibody that binds and neutralizes human CD11d and which comprises a light chain variable region (LCVR) and a heavy chain variable region (HCVR), wherein the LCVR comprises the complementarity determining regions (CDRs) LCDR1, LCDR2 and LCDR3 and the HCVR comprises CDRs HCDR1, HCDR2 and HCDR3, wherein the amino acid sequence of LCDR1 is given by SEQ ID NO: 13, the amino acid sequence of LCDR2 is given by SEQ ID NO: 14, the amino acid sequence of LCDR3 is given by SEQ ID NO: 15, the amino acid sequence of HCDR1 is given by SEQ ID NO: 16, the amino acid sequence of HCDR2 is given by SEQ ID NO: 17, and the amino acid sequence of HCDR3 is given by SEQ ID NO: 18.

In this regard, the Xaa at position 4 of the amino acid sequence given by SEQ ID NO: 13 may be an acyclic, polar amino acid with a charged entity, such as Gin, Arg, Lys, Asp or Glu, the Xaa at position 5 of the amino acid sequence given by SEQ ID NO: 14 may be an acyclic amino acid including charged amino acids such as Asp or Glu or polar amino acids such as Ser or Thr, or non-polar amino acids such as Gly Ala, Val or Leu, the Xaa at position 6 of the amino acid sequence given by SEQ ID NO: 15 may be a neutral, hydrophobic, cyclic or acyclic amino acid such as Tip, Phe, Gly, Ala, Val, Leu or Met, the Xaa at position 8 of the amino acid sequence given by SEQ ID NO: 16 may be a neutral, polar or non-polar amino acid such as Thr, Tyr, Ser, Cys, or Gly, Ala, Val or lie, the Xaa at position 6 of the amino acid sequence given by SEQ ID NO: 17 may be an acyclic, neutral, polar amino acid such as Asn, Glu, Ser or Cys, the Xaa at position 5 of the amino acid sequence given by SEQ ID NO: 18 may be an acyclic, hydrophobic amino acid such as Ile, Val, Met or Leu, and the Xaa at position 6 of the amino acid sequence given by SEQ ID NO: 18 may be a cyclic aromatic amino acid such as Tyr, His or Phe.

According to some such embodiments of the antibody of the present invention, the Xaa at position 4 of the amino acid sequence given by SEQ ID NO: 5, the amino acid sequence of LCDR2 is given by SEQ ID NO: 6, the amino acid sequence of LCDR3 is given by SEQ ID NO: 7, the amino acid sequence of HCDR1 is given by SEQ ID NO: 8, the amino acid sequence of HCDR2 is given by SEQ ID NO: 9, and the amino acid sequence of HCDR3 is given by SEQ ID NO: 10.

According to other such embodiments of the antibody of the present invention, the Xaa at position 4 of the amino acid sequence given by SEQ ID NO: 5, the Xaa at position 5 of the amino acid sequence given by SEQ ID NO: 6 is Glu, the Xaa at position 6 of the amino acid sequence given by SEQ ID NO: 7 is Trp, the Xaa at position 8 of the amino acid sequence given by SEQ ID NO: 8 is Thr, the Xaa at position 6 of the amino acid sequence given by SEQ ID NO: 9 is Asn, the Xaa at position 5 of the amino acid sequence given by SEQ ID NO: 10 is Ile, and the Xaa at position 6 of the amino acid sequence given by SEQ ID NO: 10 is Tyr.

According to other such embodiments of the antibody of the present invention, the Xaa at position 4 of the amino acid sequence given by SEQ ID NO: 5 is Arg, the Xaa at position 5 of the amino acid sequence given by SEQ ID NO: 6 is Gly, the Xaa at position 6 of the amino acid sequence given by SEQ ID NO: 7 is Phe, the Xaa at position 8 of the amino acid sequence given by SEQ ID NO: 8 is Thr, the Xaa at position 6 of the amino acid sequence given by SEQ ID NO: 9 is Asn, the Xaa at position 5 of the amino acid sequence given by SEQ ID NO: 10 is Val, and the Xaa at position 6 of the amino acid sequence given by SEQ ID NO: 10 is His.

According to even further such embodiments of the antibody of the present invention, the Xaa at position 4 of the amino acid sequence given by SEQ ID NO: 5 is Gln, the Xaa at position 5 of the amino acid sequence given by SEQ ID NO: 6 is Glu, the Xaa at position 6 of the amino acid sequence given by SEQ ID NO: 7 is Gly, the Xaa at position 8 of the amino acid sequence given by SEQ ID NO: 8 is Thr, the Xaa at position 6 of the amino acid sequence given by SEQ ID NO: 9 is Ser, the Xaa at position 5 of the amino acid sequence given by SEQ ID NO: 10 is Ile, and the Xaa at position 6 of the amino acid sequence given by SEQ ID NO: 10 is Tyr.

According to some such embodiments of the antibody of the present invention, the Xaa at position 4 of the amino acid sequence given by SEQ ID NO: 5 is Arg, the Xaa at position 5 of the amino acid sequence given by SEQ ID NO: 6 is Gly, the Xaa at position 6 of the amino acid sequence given by SEQ ID NO: 7 is Phe, the Xaa at position 8 of the amino acid sequence given by SEQ ID NO: 8 is Tyr, the Xaa at position 6 of the amino acid sequence given by SEQ ID NO: 9 is Asn, the Xaa at position 5 of the amino acid sequence given by SEQ ID NO: 10 is Ile, and the Xaa at position 6 of the amino acid sequence given by SEQ ID NO: 10 is His.

According to other such embodiments of the antibody of the present invention, the Xaa at position 4 of the amino acid sequence given by SEQ ID NO: 5 is Glu, the Xaa at position 5 of the amino acid sequence given by SEQ ID NO: 6 is Glu, the Xaa at position 6 of the amino acid sequence given by SEQ ID NO: 7 is Trp, the Xaa at position 8 of the amino acid sequence given by SEQ ID NO: 8 is Thr, the Xaa at position 6 of the amino acid sequence given by SEQ ID NO: 9 is Ser, the Xaa at position 5 of the amino acid sequence given by SEQ ID NO: 10 is lie, and the Xaa at position 6 of the amino acid sequence given by SEQ ID NO: 10 is Tyr.

In a particular embodiment, the present invention provides an antibody that binds human CD11d, e.g. a humanized antibody, comprising a LCVR and a HCVR, wherein the amino acid sequence of the LCVR is given by SEQ ID NO: 3 and the amino acid sequence of the HCVR is given by SEQ ID NO: 4. In a further particular embodiment, the present invention provides an antibody that binds human CD11d, comprising a light chain (LC) and a heavy chain (HC), wherein the amino acid sequence of the LC is given by SEQ ID NO: 1 and the amino acid sequence of the HC is given by SEQ ID NO: 2.

The present invention also provides a method of treating CNS trauma comprising administering to a patient in need thereof an effective amount of an antibody of the present invention. According to particular embodiments, the present invention provides a method of treating one or more of SCI, TBI, and SIRS following CNS trauma comprising administering to a patient in need thereof an effective amount of an antibody of the present invention.

The present invention further provides pharmaceutical compositions comprising an antibody of the present invention and one or more pharmaceutically acceptable carriers, diluents or excipients. Further, the present invention provides a method of treating CNS trauma including spinal cord injury (SCI) and traumatic brain injury (TBI) comprising administering to a patient in need thereof an effective amount of a pharmaceutical composition of the present invention. In some embodiments, the present invention provides a method of treating systemic inflammatory response (SIRS) following a CNS trauma comprising administering to a patient in need thereof an effective amount of a pharmaceutical composition of the present invention.

The present invention also provides an antibody of the present invention for use in therapy. According to some embodiments, the present invention provides an antibody of the present invention for use in treatment of CNS trauma. In particular embodiments the CNS trauma is one or more of SCI and TBI. In some embodiments, the invention provides an antibody of the present invention for use in treatment of SIRS following CNS trauma.

In an embodiment, the present invention provides the use of an antibody of the present invention in the manufacture of a medicament for the treatment of CNS trauma. According to particular embodiments, the CNS trauma is one or more of SCI and TBI. According to some embodiments, the present invention provides the use of an antibody of the present invention in the manufacture of a medicament for the treatment of SIRS following CNS trauma.

The present invention also relates to nucleic acid molecules and expression vectors encoding an antibody of the present invention. In an embodiment, the present invention provides a DNA molecule comprising a polynucleotide sequence encoding a polypeptide having the amino acid sequence of SEQ ID NO: 1. In an embodiment, the present invention provides a DNA molecule comprising a polynucleotide sequence encoding a polypeptide having the amino acid sequence of SEQ ID NO: 2. In a further embodiment, the present invention provides a DNA molecule comprising a polynucleotide sequence encoding a polypeptide having the amino acid sequence of SEQ ID NO: 1, and comprising a polynucleotide sequence encoding a polypeptide having the amino acid sequence of SEQ ID NO: 2. In a particular embodiment the polynucleotide sequence encoding a polypeptide having the amino acid sequence of SEQ ID NO: 1 is given by SEQ ID NO: 11 and the polynucleotide sequence encoding a polypeptide having the amino acid sequence of SEQ ID NO: 2 is given by SEQ ID NO: 12.

Further, the present invention provides an antibody prepared according to a process comprising cultivating a host cell comprising a polynucleotide sequence encoding a polypeptide having the amino acid sequence of SEQ ID NO: 1 and a polynucleotide sequence encoding a polypeptide having the amino acid sequence of SEQ ID NO: 2, under conditions such that the antibody is expressed, and recovering from said host cell an antibody comprising a LC and a HC, wherein the amino acid sequence of the LC is given by SEQ ID NO: 1 and the amino acid sequence of the HC is given by SEQ ID NO: 2.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., *Ann. NY Acad. Sci.* 190: 382-93 (1971); Kabat et al., *Sequences of Proteins of Immunological Interest*, Fifth Edition, U.S. Department of Health and Human Services, NIH Publication No. 91-3242 (1991)), and North numbering convention (North et al., *A New Clustering of Antibody CDR Loop Conformations*, Journal of Molecular Biology, 406:228-256 (2011)).

LCs are classified as kappa or lambda, which are each characterized by a particular constant region as known in the art. The monoclonal antibodies of the present invention include kappa LCs. HCs are classified as gamma, mu, alpha, delta, or epsilon, and define the isotype of an antibody as IgG, IgM, IgA, IgD, or IgE, respectively. The monoclonal antibodies of the present invention include IgG HCs. IgG antibodies can be further divided into subclasses, e.g., IgG1, IgG2, IgG3, IgG4. In a particular embodiment, the monoclonal antibodies of the present invention are IgG4. The carboxy-terminal portion of each HC defines a constant region primarily responsible for effector function.

According to a further embodiment, a humanized antibody is provided which exhibits a particular binding affinity for CD11d. In one embodiment, the humanized antibody exhibits a binding affinity for rat CD11d in the range of about 0.05 to 5.0 nM. Such humanized antibodies also exhibit a binding affinity for human CD11d. Preferably, the antibody exhibits a binding affinity for rat CD11d of less than 0.1, 0.2, 0.3, 0.4 or 0.5 nM and greater than 4.5, 4.0, 3.5, 3.0, 2.5, 2.0 or 1.5 nM. Thus, in one preferred embodiment, the antibody exhibits a binding affinity for rat CD11 d in the range of about 0.5-2.0 nM. Thus, CD11 d binding affinities which are higher and lower than these ranges may decrease the therapeutic utility of the antibody, for example, may result in significantly reduced anti-inflammatory properties. The humanized antibody exhibiting such binding affinities for CD11d may be based on human IgG, such as human IgG4, having variable CDRs such as the LCDRs of SEQ ID NO: 13, 14 and 15 and the HCDRs of SEQ ID NO: 16, 17 and 18, and preferably the LCDRs of SEQ ID NO: 5, 6 and 7 and the HCDRs of SEQ ID NO: 8, 9 and 10.

CD11d Antibody Expression

The antibodies of the present invention may be prepared and purified using known methods, e.g. genetic engineering. Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. Each of the light chains and the heavy chains may be expressed independently from different promoters to which they are operably linked in one vector or, alternatively, they each may be expressed independently from different promoters to which they are operably linked in two vectors—one expressing the light chain and one expressing the heavy chain. Exemplary suitable vectors for use in preparing antibodies of the present invention are known and include vectors such as are available from Lonza Biologics.

A particular DNA polynucleotide sequence encoding an exemplified light chain of an exemplified CD11d antibody of the present invention having the amino acid sequence of SEQ ID NO: 1 is provided by SEQ ID NO: 11. A particular DNA polynucleotide sequence encoding an exemplified heavy chain of a CD11d antibody of the present invention having the amino acid sequence of SEQ ID NO: 2 is provided by SEQ ID NO: 12.

A host cell includes cells stably or transiently transfected, transformed, transduced, or infected with one or more expression vectors expressing a light chain, a heavy chain or both a light and heavy chain of the present invention. Creation and isolation of host cell lines producing a CD11d antibody of the present invention can be accomplished using standard techniques known in the art, Mammalian cells are preferred host cells for expression of fusion compounds of the present invention. Particular mammalian cells include CHO and NS0. As one of skill in the art will appreciate, mammalian expression of antibodies will result in glycosylation, typically at highly conserved N-glycosylation sites in the Fe region.

CD11d antibodies of the present invention may be secreted into the medium, for example medium in which the host cells are cultured, and the antibodies can be recovered therefrom or purified by conventional techniques. For example, the antibodies may be recovered from the medium using Protein A or G affinity chromatography, size exclusion chromatography or Capto multimodal chromatography, using conventional methods. Additionally, soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

Pharmaceutical Composition

CD11d antibodies of the present invention may be administered to a patient alone or in combination with a pharmaceutically or physiologically acceptable carrier in single or multiple doses. The expressions "pharmaceutically acceptable" or "physiologically acceptable" mean acceptable for use in the pharmaceutical and veterinary arts, i.e. not being unacceptably toxic or otherwise unsuitable for physiological use.

The antibodies of the present invention are intended for administration via any suitable route of administration, and pharmaceutical compositions comprising the antibodies are, thus, designed to be appropriate for the selected mode of administration. Pharmaceutically acceptable diluents, carriers, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington, The Science and Practice of Pharmacy,* 19$^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with an antibody of the present invention, retains the molecule's activity and is non-reactive with the patient's immune system. A pharmaceutical composition of the present invention comprises a compound and one or more pharmaceutically acceptable carriers, diluents, or excipients.

In one embodiment, the present antibodies are formulated for administration via parenteral routes including intravenous, subcutaneous, intraperitoneal or intramuscular, and thus, are formulated in a medical-grade, physiologically acceptable carrier, such as an aqueous solution in sterile and pyrogen-free form, optionally, buffered or made isotonic. The carrier may be distilled water, a sterile carbohydrate-containing solution (e.g. sucrose or dextrose) or a sterile saline solution comprising sodium chloride and optionally buffered. Suitable sterile saline solutions may include varying concentrations of sodium chloride, for example, normal saline (0.9%), half-normal saline (0.45%), quarter-normal saline (0.22%), and solutions comprising greater amounts of sodium chloride (e.g. 3%-7%, or greater). Saline solutions may optionally include additional components, e.g. carbohydrates such as dextrose and the like. Examples of saline solutions including additional components, include Ringer's solution, e.g. lactated or acetated Ringer's solution, phosphate buffered saline (PBS), TRIS (hydroxymethyl) aminomethane hydroxymethyl) aminomethane)-buffered saline (TBS), Hank's balanced salt solution (HBSS), Earle's balanced solution (EBSS), standard saline citrate (SSC), HEPES-buffered saline (HBS) and Gey's balanced salt solution (GBSS).

In other embodiments, the present antibodies are formulated for administration by routes including, but not limited to, oral, intranasal, enteral, topical, sublingual, intra-arterial, intramedullary, intrauterine, intrathecal, inhalation, ocular, transdermal, vaginal or rectal routes, and will include appropriate carriers in each case. For oral administration, antibodies may be formulated in normal saline, complexed with food, in a capsule or in a liquid formulation with an emulsifying agent. For topical application creams, lotions and ointments may be prepared using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, anti-microbial agents, anti-oxidants and other preservatives may be added to the composition to prevent microbial growth and/or degradation over prolonged storage periods.

Therapeutic Uses

An effective amount of an antibody or pharmaceutical composition of the present invention refers to an amount necessary (at dosages and for periods of time and for the means of administration) to achieve the desired therapeutic result or treatment. An effective amount of the antibody or pharmaceutical composition thereof may vary according to factors such as the disease state, age, sex, and weight of the individual, and the ability of the antibody or portion(s) thereof to elicit a desired response in the individual. An effective amount is also one in which any toxic or detrimental effect of the antibody of pharmaceutical composition is outweighed by the therapeutically beneficial effects. Generally, an effective amount of an antibody is an amount in the range of about 1 mg/kg to 100 mg/kg, preferably 1 mg/kg to 10 mg/kg.

As used herein, "treatment" and/or "treating" are intended to refer to all processes wherein there may be a slowing, interrupting, arresting, controlling, or stopping of the progression of the disorders described herein (for example, CNS trauma such as SCI and TBI, as well as SIRS following CNS trauma), but does not necessarily indicate a total elimination of all disorder symptoms. Treatment includes administration of a CD11d antibody of the present invention, or pharmaceutical composition thereof, for treatment of a disease or condition in a patient that would benefit from a decreased level, or decreased bioactivity, of CD11d. Treatment includes: (a) inhibiting further progression of the disease, i.e., inhibiting CNS trauma and/or arresting complications associated with TBI, SCI and/or SIRS following CNS trauma; and (b) relieving the disease, i.e., causing regression of, or alleviating symptoms or complications of CNS trauma such as TBI, SCI and/or SIRS following CNS trauma. CD11d antibodies of the present invention are expected to be useful in the treatment of CNS trauma, such as one of TBI and SCI, and/or SIRS following CNS trauma.

The terms "patient," "subject," and "individual," used interchangeably herein, refer to an animal, including humans and non-human mammals, and preferably the term refers to humans. In some embodiments, the subject has been diagnosed as "in need of" or being "at risk of" needing or in need of treatment for CNS trauma including TBI and SCI, and/or SIRS following CNS trauma.

The following Examples, which exemplify CD11d antibodies of the present invention for treating CNS trauma such as SCI and TBI, and/or SIRS following CNS trauma, are set forth by way of illustration and not limitation. It should be understood that various modifications may be made by one of ordinary skill in the art.

EXAMPLES

Example 1—Antibody Screening Study

Binding Affinity—Preliminary characterization of the 217L mAb reveals an affinity of ~1.9 nM for human CD11d as determined using a flow cytometry-based assay, and a conformational epitope located within the I domain. To determine the desired characteristics of a humanized antibody, it was first determined if a higher affinity to CD11d translates to better efficacy in vivo. The affinity of 217L mAb for CD11d was compared to the affinity of a number of similar monoclonal antibodies to rat and human CD11d. The results are set out below in Table 1:

TABLE 1

| Antibody | Estimated Kd on Rat CD11d (nM) | Estimated Kd on Human CD11d (nM) |
| --- | --- | --- |
| 217L | 4.42 | 1.87 |
| CB1 | 0.86 | 0.82 |
| CB6 | 0.45 | 0.65 |
| 226C | 0.33 | 3.65 |
| 236B | 0.36 | 2.19 |
| 236K | 0.62 | 2.40 |
| 236F | 0.77 | 2.93 |
| 236G | 1.40 | 2.95 |
| 236M | 2.95 | 0.29 |
| 236C | 3.46 | 1.52 |

The antibodies were secreted by one of hybridoma 217L (American Type Culture Collection Accession No: HB-12701), hybridoma 226C (American Type Culture Collection Accession No: HB-12592) or hybridoma 236G (American Type Culture Collection Accession No: HB-12593), or derived from 217L.

Myeloperoxidase Activity 24 hr Post-Injury in a SCI Model

Next, the effect of mAb affinity for CD11d on MPO activity (reflects quantity of neutrophils present) 24 hr post-injury in the injured rat spinal cord was determined. MPO activity is assessed by homogenizing individual spinal cord sections on ice with 5 volumes (w/v) of 50 mM potassium phosphate buffer and 5 volumes (w/v) of 0.5% hexadecyltrimethylammonium bromide (to extract the MPO from the neutrophil granules). Homogenates are centrifuged at 10,621 g for 20 min. Supernatant is removed and pellet is saved. MPO activity in the supernatant is determined by addition of 0.3 mL potassium phosphate buffer solution containing 1.25 mg/mL r-dianisidine dihydrochloride and 0.05% hydrogen peroxide. Samples from individual animal are assayed in duplicate. The colorimetric enzymatic activity reaction is started by adding 0.1 mL of sample; development of colorimetric reaction is stopped after five minutes by adding 0.1 mL 0.1% sodium azide. Absorbance is measured at 460 nm, A standard curve is also prepared using eight dilutions (0.001, 0.01, 0.03, 0.06, 0.125, 0.25, 0.5, and 1.0) of 1.0 unit/100 µl stock solution of purified human MPO (50 units/mg lyophilized protein, Sigma-Aldrich, St. Louis, Mo.). MPO activity of assayed samples is represented as relative activity units per milligram of tissue. Protein concentration of assayed samples is determined using the modified Bradford method (Bio-Rad, Protein assay kit II; Bio-Rad, Hercules, Calif.) with bovine serum albumin as the standard.

Three mAb, 217L, 236G and 226C (shaded in table above), with binding affinities to rat CD11d of 4.42, 1.40 and 0.33 nM, respectively, were selected to undergo a neuroprotection efficacy screening study. The purpose of this study was to determine whether the administration of higher affinity CD11d mAb leads to greater neuroprotection in spinal cord-injured rats. This study had the following treatment groups: Group 1, isotype-matched antibody control (1B7); Group 2, 217L mAb; Group 3, 236G mAb; Group 4, 226C mAb. Rats (n=18 per group) were given a clip-compression SCI at the 4th thoracic spinal cord segment using a 35 g clip. Three doses, 0.5, 1.0 and 3.0 mg/Kg, of antibody were tested in each group (n=6 per dose). Rats received their mAb treatment by iv injection at 2 hr post-injury. At 24 hr post-injury the rats were anesthetized, perfused with cold saline and a 0.5 cm segment of spinal cord centered on the lesion site was removed for analyses. The tissue was homogenized and assayed for myeloperoxidase (MPO), an established marker for activated neutrophils and, to a lesser extent, macrophages.

Results

Figure 3:
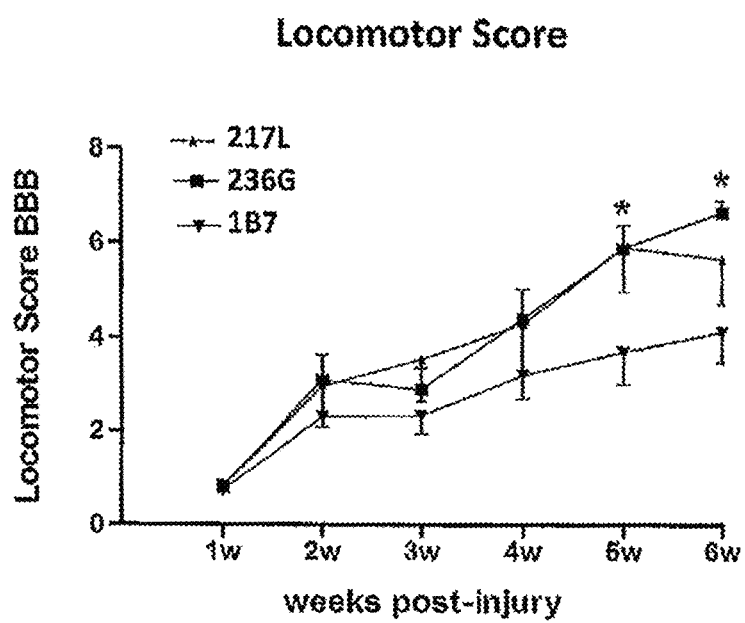
FIG. 3 graphically illustrates that, following experimentally induced SCI, rats treated with 3 mg/kg of 217L or 236G demonstrate improved hind-limb locomotor recovery after SCI (two-way ANOVA, $p<0.05$).

The 217L and the 236G mAb-treated rats recovered better locomotor activity than the 1B7 isotype control mAb-treated rats following SCI. The improved locomotor scores in 217L and 236G mAb-treated rats reached statistical significance at 5 weeks post-SCI and stayed significantly different at 6 weeks post-SCI for 236G (FIG. 3).

The above study unexpectedly illustrates that monoclonal antibodies exhibiting a particular binding affinity to rat CD11d, e.g., of less than 1.4 nM and greater than 4.4 nM, resulted in in vivo activity, such as improved neurological outcomes. This was unexpected since higher affinity mAb (such as 226C) are generally expected to be at least as if not more effective than mAb with lower affinities (such as 217L and 236G).

Example 2—Expression of Engineered CD11d Antibody

Engineered CD11d antibodies of the present invention can be expressed and purified essentially as follows. A glutamine synthetase (GS) expression vector containing a DNA molecule encoding a LC amino acid sequence of SEQ ID NO: 1 and a DNA molecule encoding a HC amino acid sequence of SEQ ID NO: 2 is used to transfect a Chinese hamster ovary cell line (CHO) by electroporation. For example, a DNA molecule having the polynucleotide sequence set forth in SEQ ID NO: 11 (wherein, n at pos. 79 is c; n at pos. 80 is a; n at pos. 81 is a; n at pos. 158 is a; n at pos. 280 is g; n at pos. 281 is g; and n at pos. 282 is g) encoding the LC of exemplified CD11d Antibody 3 of Table 2, and a DNA molecule having the polynucleotide sequence set forth in SEQ ID NO: 12 (wherein, n at pos. 88 is a; n at pos. 89 is c; n at pos. 90 is c; n at pos. 163 is t; n at pos. 164 is c; n at pos. 301 is a; n at pos. 303 is c; n at pos. 304 is t; and n at pos. 306 is c) encoding the HC of exemplified CD11d Antibody 3 of Table 2 may be used. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The master wells are screened for antibody expression and then scaled up in serum-free, suspension cultures to be used for production. Clarified medium, into which the antibody has been secreted, is applied to a Protein A affinity column that has been equilibrated with a compatible buffer, such as phosphate buffered saline (pH 7.4). The column is washed with 1 M NaCl to remove nonspecific binding components. The bound antibody is eluted, for example, with sodium citrate at pH (approx.) 3.5 and fractions are neutralized with IM Tris buffer. Antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. Engineered CD11d antibodies of the present invention may be concentrated and/or sterile filtered using common techniques. The purity of CD11d antibodies after these chromatography steps is greater than 95%. CD11d antibodies of the present invention may be immediately frozen at −70° C. or stored at 4° C. for several months.

Exemplified CD11d antibodies of the present invention, which were prepared following procedures essentially as described above, are presented in Table 2. The exemplified CD11d antibodies of Table 2 comprise a LC having an amino acid sequence given by SEQ ID NO: 1 and a HC having an amino acid sequence given by SEQ ID NO: 2, wherein residues denoted Xaa at specific positions are set forth in Table 2. Numbering of amino acids applies linear numbering: Xaa at pos. 27 of SEQ ID NO: 1 corresponds to Xaa at pos. 4 of SEQ ID NO: 5; Xaa at pos. 53 of SEQ ID NO: 1 corresponds to Xaa at pos. 5 of SEQ ID NO: 6; Xaa at pos. 94 of SEQ ID NO: 1 corresponds to Xaa at 6 of SEQ ID NO: 7; Xaa at pos. 30 of SEQ ID NO: 2 corresponds to Xaa at pos. 8 of SEQ ID NO: 8; Xaa at pos. 55 of SEQ ID NO: 2 corresponds to Xaa at pos. 6 of SEQ ID NO: 9; Xaa at pos. 101 of SEQ ID NO: 2 corresponds to Xaa at pos, 5 of SEQ ID NO: 10; and Xaa at pos. 102 of SEQ ID NO: 2 corresponds to Xaa at pos. 6 of SEQ ID NO: 10.

TABLE 2

Exemplified Engineered CD11d Antibodies of the Present Invention.

| Molecule | Exemplified LC (SEQ ID NO: 1) | Exemplified HC (SEQ ID NO: 2) |
|---|---|---|
| Exemplified Antibody 1 | Xaa at pos. 27 is Gln<br>Xaa at pos. 53 is Glu<br>Xaa at pos. 94 is Trp | Xaa at pos. 30 is Thr<br>Xaa at pos. 55 is Asn<br>Xaa at pos. 101 is Ile<br>Xaa at pos. 102 is Tyr |
| Exemplified Antibody 2 | Xaa at pos. 27 is Arg<br>Xaa at pos. 53 is Gly<br>Xaa at pos. 94 is Phe | Xaa at pos. 30 is Gly<br>Xaa at pos. 55 is Asn<br>Xaa at pos. 101 is Val<br>Xaa at pos. 102 is His |
| Exemplified Antibody 3 | Xaa at pos. 27 is Gln<br>Xaa at pos. 53 is Glu<br>Xaa at pos. 94 is Gly | Xaa at pos. 30 is Thr<br>Xaa at pos. 55 is Ser<br>Xaa at pos. 101 is Ile<br>Xaa at pos. 102 is Tyr |
| Exemplified Antibody 4 | Xaa at pos. 27 is Arg<br>Xaa at pos. 53 is Gly<br>Xaa at pos. 94 is Phe | Xaa at pos. 30 is Tyr<br>Xaa at pos. 55 is Asn<br>Xaa at pos. 101 is Ile<br>Xaa at pos. 102 is His |
| Exemplified Antibody 5 | Xaa at pos. 27 is Glu<br>Xaa at pos. 53 is Glu<br>Xaa at pos. 94 is Trp | Xaa at pos. 30 is Thr<br>Xaa at pos. 55 is Ser<br>Xaa at pos. 101 is Ile<br>Xaa at pos. 102 is Tyr |

Binding Affinity

Binding affinity of the exemplified CD11d antibodies of Table 2 were determined, for both human and rat CD11d, by Fluorescence Activated Cell Sorting (FACS) analysis. JY cells expressing human CD11d/CD18 or JY cells transfected with full-length rat CD11d are suspended in FACS buffer with goat IgG (1 mg/ml). The cell solution is added to wells of 96-well round-bottom plates at a density of $4.0 \times 10^4$ cells in 50 μL solution. Each of the exemplified CD11d antibodies of Table 2 (25 μL) or isotype control antibody (25 μL) is added to a respective well at 1:3 dilutions at final concentrations ranging between 4.6 ng/mL to 10 μg/mL. The plates are incubated on ice for 30 minutes, after which 200 μL of FACS buffer is added, plates are centrifuged at 2000 rpm for 3 minutes, and the liquid is discarded. Cells are re-suspended with 50 μL of a phycoerythrin-conjugated antibody (Jackson ImmunoResearch p/n. 709-116-149) at a 1:150 dilution and incubated on ice for 20 minutes. FACS buffer is added (200 μL) to each well and plates are spun at 2000 rpm for 3 minutes. The liquid is discarded, cells are washed with 200 μL FACS buffer, re-suspended in 120 μL of 1% paraformaldehyde in PBS, and transferred to 96-well flat-bottom plates.

Stained cells are analyzed by flow cytometry with the gate set on the isotype control antibody. The specific percent gated is calculated as [% gated (test antibody)−% gated (isotype control antibody)]. Kd determinations were made based on a non-linear regression, one-site binding model. Following procedures essentially as described above, binding affinities of the exemplified CD11d antibodies of Table 2 to human and rat CD11d were obtained.

TABLE 3

Binding Affinities of Exemplified CD11d Antibodies of Table 2 to Human and Rat CD11d

| Exemplified CD11d Antibody of Table 2 | Human Kd (nM) | Rat Kd (nM) |
|---|---|---|
| Antibody 1 | 0.4358 | 1.453 |
| Antibody 2 | 0.3031 | 0.1329 |
| Antibody 3 | 0.3041 | 0.6775 |
| Antibody 4 | 0.3327 | 0.2466 |
| Antibody 5 | 0.3436 | 1.184 |

The data presented in Table 3 shows the binding affinities of the exemplified humanized CD11d antibodies of the present invention, to rat CD11d of about 0.13 nM to about 1.45 nM. The data also demonstrates that each of the exemplified CD11d humanized antibodies also bound to human CD11d and possessed binding affinities in the range of about 0.3 nM to about 0.50 nM.

In Vivo Inflammatory Response Analysis in Rat SCI Model

Myeloperoxidase (MPO) activity (marker of neutrophils) and ED-1 expression (marker of phagocytic macrophages) in rat SCI model was used to assess the degree of inflammation following SCI. Experimental SCI is introduced in 84 female Wistar rats (Charles River, St. Constant, Quebec), weighing 210-250 grams and aged approx. 7-8 weeks, by spinal clip compression at the eight thoracic vertebra (T8). Rats are divided into treatment groups (treatment with exemplified CD11d antibodies of Table 2), an isotype control group, or a non-SCI control group (n=6 per group) and are further divided into 24 hour (n=42) and 72 hour (n=42) treatment groups (as represented in Table 4 below).

Two hours post SCI, rats in the 24 hour treatment group receive a single tail vein injection of one of: a.) 1 mg/kg exemplified Antibody 1; b.) 1 mg/kg exemplified Antibody 2; c.) 1 mg/kg exemplified Antibody 3; d.) 1 mg/kg exemplified Antibody 4; e.) 1 mg/kg exemplified Antibody 5; or f.) 1 mg/kg exemplified IgG4 isotype control. Rats in the 72 hour treatment group receive a tail vein injection of one of treatments a.) through f.) (above) at 2, 24 and 72 hours post-SCI. Following respective treatment periods, rats are sacrificed. Spinal cord from the vertebral T8 region are collected from each treatment group of sacrificed rats as well as a non-SCI control group.

Following procedures essentially as described above, MPO activity and ED-1 expression in SCI rats treated with exemplified CD11d antibodies of Table 2 was obtained

TABLE 4

MPO Activity and ED-1 Expression in SCI Rats Treated with Exemplified Anti-CD11d Antibodies of Table 2

| Anti-CD11d Antibody (1 mg/kg) | MPO activity (units/mg of tissue) | | ED-1 expression (Optical Density Ratio) | |
|---|---|---|---|---|
| | 24 h post SCI (n = 42) | 72 h post SCI (n = 42) | 24 h post SCI (n = 42) | 72 h post-SCI (n = 42) |
| No treatment (uninjured animals) | 6.91 ± 0.91 | 6.91 ± 0.91 | 0.477 ± 0.10 | 0.477 ± 0.10 |
| Isotype Control | 98.10 ± 7.61 | 48.60 ± 4.20 | 3.40 ± 0.32 | 4.50 ± 0.50 |
| Antibody 1 | 67.30 ± 8.21 | 32.70 ± 1.60 | 2.07 ± 0.26 | 1.97 ± 0.21 |
| Antibody 2 | 63.10 ± 5.35 | 29.40 ± 2.72 | 1.83 ± 0.14 | 2.43 ± 0.15 |
| Antibody 3 | 54.10 ± 0.89 | 26.51 ± 0.80 | 1.56 ± 0.15 | 2.20 ± 0.13 |
| Antibody 4 | 71.16 ± 5.67 | 31.85 ± 0.81 | 2.13 ± 0.19 | 2.00 ± 0.27 |
| Antibody 5 | 65.73 ± 9.84 | 30.63 ± 1.66 | 2.06 ± 0.19 | 2.39 ± 0.12 |

The results presented in Table 4 illustrate a reduction in MPO activity and ED-1 expression (from spinal cord-injured tissue) in SCI rats treated with exemplified CD11d antibodies of Table 2 as compared to SCI rats treated with isotype control antibody.

Functional Locomotor Capacity Assessment In Vivo in Rat SCI Model

The Basso, Beattie, Bresnahan (BBB) scale is used for a functional evaluation of locomotor capacity recovery following SCI introduction in rat. The BBB is a semiquantitative scale based on locomotor response of rats that have values ranging from zero to 21. The scale (0-21) represents sequential recovery stages and categorizes combinations of rat hindlimb joint movement, hindlimb movements of all three joints (but no stepping), stepping, forelimb and hindlimb coordination, trunk position and stability, paw placement and tail position. In general: a score of 0-7 is indicative of a rat having no hindlimb joint movement or isolated hindlimb joint movements of 1 to 3 joints but no stepping; a score of 8-13 means a rat has intervals of uncoordinated stepping with increasing degrees of weight support; and a score of 14-21 indicates a rat has forelimb and hindlimb coordination.

Experimental SCI is introduced in female Wistar rats (Charles River, St. Constant, Quebec), aged approx. 7-8 weeks and weighing 250-300 grams, by spinal clip compression at the eight thoracic vertebra (T8). Rats are divided into two treatment groups, and are administered a single tail vein injection of either a.) 1 mg/kg exemplified CD11d Antibody 3 of Table 2 (n=9), or b.) 1 mg/kg IgG4 isotype control (n=10), at 2, 24 and 48 hours post-SCI introduction. Observers (n=3), blinded to the rat treatment group, perform BBB scoring of locomotor recovery at each week for 10 weeks post SCI introduction.

Following procedures essentially as described above, functional locomotor capacity assessment (per BBB scale) in SCI rats treated with exemplified CD11d Antibody 3 of Table 2 was obtained. Results are provided in Table 5 (results analyzed by two way ANOVA).

TABLE 5

Functional Locomotor Capacity (BBB scale) in SCI Rats Treated with Exemplified CD11d Antibody 3 of Table

| Time (weeks) Post-SCI | Control Antibody | CD11d Antibody |
|---|---|---|
| 1 | 1.05 ± 0.29 | 1.0 ± 0.2 |
| 2 | 2.05 ± 0.32 | 3.70 ± 0.60* |
| 3 | 3.60 ± 0.34 | 6.30 ± 0.52* |
| 4 | 5.80 ± 0.36 | 7.00 ± 0.28* |
| 5 | 5.95 ± 0.46 | 7.40 ± 0.35* |
| 6 | 6.86 ± 0.18 | 8.10 ± 0.39* |
| 7 | 7.05 ± 0.20 | 8.40 ± 0.40* |
| 8 | 7.30 ± 0.20 | 8.50 ± 0.47* |
| 10 | 7.23 ± 0.26 | 8.60 ± 0.51* |

No data obtained in week 9;
*P < 0.01

The results presented in Table 5 demonstrate rats administered Exemplified Antibody 3 of Table 2 achieve functional locomotor capacity more quickly and to a greater extent compared to isotype control treated rats with SCI. Rats treated with Exemplified Antibody 3 of Table 2 displayed a significant treatment effect (P=0.0029), a significant effect of time (P<0.0001), and a significant interaction of treatment and time (P=0.0006) in comparison to rats treated with isotype control antibody.

Sequences

Exemplified LC (SEQ ID NO: 1)
DIQMTQSPSSLSASVGDRVTITCRASXaaSIGTRIHWYQQKPGKAPKLLIYFASXaaSISG
VPSRFSGSGSGTDFTLTISSLQPEDFATYYCQQSKIXaaPTTFGGGTKLEIKRTVAAPSV
FIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC, wherein Xaa at pos. 27
is Gln, Arg, or Glu; Xaa at pos. 53 is Glu or Gly; and Xaa at pos. 94 is Trp, Phe, or Gly Exemplified HC (SEQ ID NO: 2)
QVQLVQSGAEVKKPGASVKVSCKASGYTFXaaDYNMHWVRQAPGQGLEWMGYIYP
YXaaGDTGYNQNFKSRVTMTRDTSTSTVYMELSSLRSEDTAVYYCARGLXaaXaaYGY
LNVAMDSWGQGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDK
RVESKYGPPCPPCPAPEAAGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLP
SSIEKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSLS
LG, wherein Xaa at pos. 30 is Thr, Tyr, or Gly; Xaa at pos. 55 is Asn or Ser; Xaa at pos. 101
is Ile or Val; Xaa at pos. 102 is Tyr or His Exemplified LCVR (SEQ ID NO: 3)
DIQMTQSPSSLSASVGDRVTITCRASXaaSIGTRIIIWYQQKPGKAPKLLIYFASXaaSISG
VPSRFSGSGSGTDFTLTISSLQPEDFATYYCQQSKIXaaPTTFGGGTKLEIK, wherein Xaa
at pos. 27 is Gln, Arg, or Glu; Xaa at pos. 53 is Glu or Gly; and Xaa at pos. 94 is Trp,
Phe, or Gly Exemplified HCVR (SEQ ID NO: 4)
QVQLVQSGAEVKKPGASVKVSCKASGYTFXaaDYNMHWVRQAPGQGLEWMGYIYP
YXaaGDTGYNQNFKSRVTMTRDTSTSTVYMELSSLRSEDTAVYYCARGLXaaXaaYGY
LNVAMDSWGQGTLVTVSS, wherein Xaa at pos. 30 is Thr, Tyr, or Gly; Xaa at pos. 55 is
Asn or Ser; Xaa at pos. 101 is Ile or Val; Xaa at pos. 102 is Tyr or His Exemplified LCDR1 (SEQ ID NO: 5)
RASXaaSIGTRIH, wherein Xaa at pos. 4 is Gln, Arg, or Glu Exemplified LCDR2 (SEQ ID NO: 6)
YFASXaaSIS, wherein Xaa at pos. 5 is Glu or Gly Exemplified LCDR3 (SEQ ID NO: 7)
QQSKIXaaPTT, wherein Xaa at pos. 6 is Trp, Phe, or Gly Exemplified HCDR1 (SEQ ID NO: 8)
KASGYTFXaaDYNMH, wherein Xaa at pos. 8 is Thr, Tyr, or Gly Exemplified HCDR2 (SEQ ID NO: 9)
YIYPYXaaGDTGYNQNFKS, wherein Xaa at pos. 6 is Asn or Ser Exemplified HCDR3 (SEQ ID NO: 10)
ARGLXaaXaaYGYLNVAMDS, wherein Xaa at pos. 5 is Ile or Val; Xaa at pos. 6 is Tyr or
His Nucleotide Sequence Encoding the Exemplified LC given by SEO ID NO: 1
(SEQ ID NO: 11)
gacatccaga tgacccagtc tccatcctcc ctgtctgcat ctgtaggaga cagagtcacc
atcacttgca gggccagtnn nagcattggc acaagaatac actggtatca gcagaaacca
gggaaagccc ctaagctcct gatctatttt gcttctgngt ctatctctgg agtcccatca
aggttcagtg gcagtggatc tgggacagat ttcactctca ccatcagcag cctgcagcct
gaagattttg caacttacta ctgtcaacaa agtaaaatcn nnccaacgac gttcggcgga
gggaccaagc tggagatcaa acgaactgtg gctgcaccat ctgtcttcat cttcccgcca
tctgatgagc agttgaaatc tggaactgcc tctgttgtgt gcctgctgaa taacttctat
cccagagagg ccaaagtaca gtggaaggtg gataacgccc tccaatcggg taactcccag
gagagtgtca cagagcagga cagcaaggac agcacctaca gcctcagcag caccctgacg
ctgagcaaag cagactacga gaaacacaaa gtctacgcct gcgaagtcac ccatcagggc
ctgagctcgc ccgtcacaaa gagcttcaac aggggagagt gc
wherein, n at pos. 79 is c, a, or g; n at pos, 80 is a or g; n at pos. 81 is a or g; n at
pos. 158 is a or g; n at pos. 280 is g or t; n at pos, 281 is g or t; and n at pos. 282 is
g or t.

Nucleotide Sequence Encoding the Exemplified HC given by SEO ID NO: 2
(SEQ ID NO: 12)
caggtgcagc tggtgcagtc tggtgctgaa gtgaagaagc ctggggcctc agtgaaggtg
tcctgcaagg catctggata cacattcnnn gactacaaca tgcactgggt gcgacaggcc

| Sequences |
|---|
| cctggacaag ggcttgagtg gatgggatat atttatcctt acnntggtga tactgggtac<br>aaccagaatt tcaagagcag agtcaccatg accagggaca cgtccacgag cacagtctac<br>atggagctga gcagcctgag atctgaggac acggccgtgt attactgtgc gagaggatta<br>ntnnantacg gctaccttaa cgttgctatg gactcctggg gccaagggac actagtcaca<br>gtctcctcag cctccaccaa gggcccatcg gtcttccccg tagcgccctg ctccaggagc<br>acctccgaga gcacagccgc cctgggctgc ctggtcaagg actacttccc cgaaccggtg<br>acggtgtcgt ggaactcagg cgccctgacc agcggcgtgc acaccttccc ggctgtccta<br>cagtcctcag gactctactc cctcagcagc gtggtgaccg tgccctccag cagcttgggc<br>acgaagacct acacctgcaa cgtagatcac aagcccagca acaccaaggt ggacaagaga<br>gttgagtcca aatatggtcc cccatgccca ccctgcccag cacctgaggc cgccggggga<br>ccatcagtct tcctgttccc cccaaaaccc aaggacactc tcatgatctc ccggacccct<br>gaggtcacgt gcgtggtggt ggacgtgagc caggaagacc ccgaggtcca gttcaactgg<br>tacgtggatg gcgtggaggt gcataatgcc aagacaaagc cgcgggagga gcagttcaac<br>agcacgtacc gtgtggtcag cgtcctcacc gtcctgcacc aggactggct gaacggcaag<br>gagtacaagt gcaaggtctc caacaaaggc ctcccgtcct ccatcgagaa aaccatctcc<br>aaagccaaag ggcagccccg agagccacag tgtacaccc tgcccccatc ccaggaggag<br>atgaccaaga accaggtcag cctgacctgc ctggtcaaag gcttctaccc cagcgacatc<br>gccgtggagt gggaaagcaa tgggcagccg gagaacaact acaagaccac gcctcccgtg<br>ctggactccg acggctcctt cttcctctac agcaggctaa ccgtggacaa gagcaggtgg<br>caggagggga atgtcttctc atgctccgtg atgcatgagg ctctgcacaa ccactacaca<br>cagaagagcc tctccctgtc tctgggt<br>wherein, n at pos. 88 is a, g, or t; n at pos. 89<br>is a or t; n at pos. 164 is a or c; n at pos, 301 is a or g; n at pos. 303 is c or t; n at<br>pos. 304 is t or c; and n at pos. 306 is c or t |

---

We claim:

1. An antibody that binds human CD11d comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is given by SEQ ID NO: 5, the amino acid sequence of LCDR2 is given by SEQ ID NO: 6, the amino acid sequence of LCDR3 is given by SEQ ID NO: 7, the amino acid sequence of HCDR1 is given by SEQ ID NO: 8, the amino acid sequence of HCDR2 is given by SEQ ID NO: 9, and the amino acid sequence of HCDR3 is given by SEQ ID NO: 10.

2. The antibody of claim 1, comprising a light chain variable region (LCVR) and a heavy chain variable region (HCVR), wherein the amino acid sequence of the LCVR is given by SEQ ID NO: 3 and the amino acid sequence of the HCVR is given by SEQ ID NO: 4.

3. The antibody of claim 1, comprising a light chain (LC) and a heavy chain (HC), wherein the amino acid sequence of the LC is given by SEQ ID NO: 1 and the amino acid sequence of the HC is given by SEQ ID NO: 2.

4. The antibody of claim 1, wherein:
Xaa at position 4 of the amino acid sequence given by SEQ ID NO: 5 is Gln;
Xaa at position 5 of the amino acid sequence given by SEQ ID NO: 6 is Glu;
Xaa at position 6 of the amino acid sequence given by SEQ ID NO: 7 is Trp;
Xaa at position 8 of the amino acid sequence given by SEQ ID NO: 8 is Thr;
Xaa at position 6 of the amino acid sequence given by SEQ ID NO: 9 is Asn;
Xaa at position 5 of the amino acid sequence given by SEQ ID NO: 10 is Ile; and
Xaa at position 6 of the amino acid sequence given by SEQ ID NO: 10 is Tyr.

5. The antibody of claim 1, wherein:
Xaa at position 4 of the amino acid sequence given by SEQ ID NO: 5 is Arg;
Xaa at position 5 of the amino acid sequence given by SEQ ID NO: 6 is Gly;
Xaa at position 6 of the amino acid sequence given by SEQ ID NO: 7 is Phe;

Xaa at position 8 of the amino acid sequence given by SEQ ID NO: 8 is Thr;
Xaa at position 6 of the amino acid sequence given by SEQ ID NO: 9 is Asn;
Xaa at position 5 of the amino acid sequence given by SEQ ID NO: 10 is Val; and
Xaa at position 6 of the amino acid sequence given by SEQ ID NO: 10 is His.

6. The antibody of claim 1, wherein:
Xaa at position 4 of the amino acid sequence given by SEQ ID NO: 5 is Gln;
Xaa at position 5 of the amino acid sequence given by SEQ ID NO: 6 is Glu;
Xaa at position 6 of the amino acid sequence given by SEQ ID NO: 7 is Gly;
Xaa at position 8 of the amino acid sequence given by SEQ ID NO: 8 is Thr;
Xaa at position 6 of the amino acid sequence given by SEQ ID NO: 9 is Ser;
Xaa at position 5 of the amino acid sequence given by SEQ ID NO: 10 is Ile; and
Xaa at position 6 of the amino acid sequence given by SEQ ID NO: 10 is Tyr.

7. The antibody of claim 1, wherein:
Xaa at position 4 of the amino acid sequence given by SEQ ID NO: 5 is Arg;
Xaa at position 5 of the amino acid sequence given by SEQ ID NO: 6 is Gly;
Xaa at position 6 of the amino acid sequence given by SEQ ID NO: 7 is Phe;
Xaa at position 8 of the amino acid sequence given by SEQ ID NO: 8 is Tyr;
Xaa at position 6 of the amino acid sequence given by SEQ ID NO: 9 is Asn;
Xaa at position 5 of the amino acid sequence given by SEQ ID NO: 10 is Ile; and
Xaa at position 6 of the amino acid sequence given by SEQ ID NO: 10 is His.

8. The antibody of claim 1, wherein:
Xaa at position 4 of the amino acid sequence given by SEQ ID NO: 5 is Glu;
Xaa at position 5 of the amino acid sequence given by SEQ ID NO: 6 is Glu;
Xaa at position 6 of the amino acid sequence given by SEQ ID NO: 7 is Trp;
Xaa at position 8 of the amino acid sequence given by SEQ ID NO: 8 is Thr;
Xaa at position 6 of the amino acid sequence given by SEQ ID NO: 9 is Ser;
Xaa at position 5 of the amino acid sequence given by SEQ ID NO: 10 is Ile; and
Xaa at position 6 of the amino acid sequence given by SEQ ID NO: 10 is Tyr.

9. The antibody as defined in claim 1, wherein the antibody is a humanized antibody that exhibits a binding affinity for rat CD11d in the range of 0.05 to 5.0 nM.

10. The antibody of claim 9, which exhibits a binding affinity for rat CD11d in the range of 0.13 to 2.0 nM.

11. The antibody of claim 10, which exhibits a binding affinity for human CD11d in the range of 0.3-0.5 nM.

12. The antibody of claim 9, which exhibits a binding affinity for human CD11d in the range of 0.3-0.5 nM.

13. A mammalian cell comprising a polynucleotide sequence encoding an antibody as defined in claim 1.

14. A pharmaceutical composition comprising an antibody of claim 1 and one or more pharmaceutically acceptable carriers, diluents or excipients.

15. A method of treating central nervous system trauma comprising administering to a patient in need thereof the pharmaceutical composition of claim 14.

16. A method of treating systemic inflammatory response syndrome following central nervous system trauma comprising administering to a patient in need thereof the pharmaceutical composition of claim 14.

17. A method of treating central nervous system trauma comprising administering to a patient in need thereof an effective amount of an antibody of claim 1.

18. A method of treating systemic inflammatory response syndrome following central nervous system trauma comprising administering to a patient in need thereof an effective amount of an antibody of claim 1.

\* \* \* \* \*

SEQUENCE LISTING

<160> NUMBER OF SEQ ID NOS: 18

<210> SEQ ID NO 1
<211> LENGTH: 214
<212> TYPE: PRT
<213> ORGANISM: Artificial Sequence
<220> FEATURE:
<223> OTHER INFORMATION: Exemplified LC
<220> FEATURE:
<221> NAME/KEY: MISC_FEATURE
<222> LOCATION: (27)..(27)
<223> OTHER INFORMATION: Xaa at pos. 27 is Gln, Arg, or Glu
<220> FEATURE:
<221> NAME/KEY: MISC_FEATURE
<222> LOCATION: (53)..(53)
<223> OTHER INFORMATION: Xaa at pos. 53 is Glu or Gly
<220> FEATURE:
<221> NAME/KEY: MISC_FEATURE
<222> LOCATION: (94)..(94)
<223> OTHER INFORMATION: Xaa at pos. 94 is Trp, Phe, or Gly

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Xaa Ser Ile Gly Thr Arg
            20                  25                  30

Ile His Trp Tyr Gln Gln Lys Pro Gly Lys Ala Pro Lys Leu Leu Ile
        35                  40                  45

Tyr Phe Ala Ser Xaa Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Lys Ile Xaa Pro Thr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 2
<211> LENGTH: 449
<212> TYPE: PRT
<213> ORGANISM: Artificial Sequence
<220> FEATURE:
<223> OTHER INFORMATION: Exemplified HC
<220> FEATURE:
<221> NAME/KEY: MISC_FEATURE
<222> LOCATION: (30)..(30)
<223> OTHER INFORMATION: Xaa at pos. 30 is Thr, Tyr, or Gly
<220> FEATURE:
<221> NAME/KEY: MISC_FEATURE
<222> LOCATION: (55)..(55)
<223> OTHER INFORMATION: Xaa at pos. 55 is Asn or Ser
<220> FEATURE:
<221> NAME/KEY: MISC_FEATURE
<222> LOCATION: (101)..(101)
<223> OTHER INFORMATION: Xaa at pos. 101 is Ile or Val
<220> FEATURE:
<221> NAME/KEY: MISC_FEATURE
<222> LOCATION: (102)..(102)
<223> OTHER INFORMATION: Xaa at pos. 101 is Tyr or His

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Asp Tyr
                20                  25                  30

Asn Met His Trp Val Arg Gln Ala Pro Gly Gln Gly Leu Glu Trp Met
            35                  40                  45

Gly Tyr Ile Tyr Pro Tyr Xaa Gly Asp Thr Gly Tyr Asn Gln Asn Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Xaa Xaa Tyr Gly Tyr Leu Asn Val Ala Met Asp Ser
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

-continued

```
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Glu Ser Lys
                210                 215                 220
Tyr Gly Pro Pro Cys Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly

<210> SEQ ID NO 3
<211> LENGTH: 107
<212> TYPE: PRT
<213> ORGANISM: Artificial Sequence
<220> FEATURE:
<223> OTHER INFORMATION: Exemplified LCVR
<220> FEATURE:
<221> NAME/KEY: MISC_FEATURE
<222> LOCATION: (27)..(27)
<223> OTHER INFORMATION: Xaa at pos. 27 is Gln, Arg, or Glu
<220> FEATURE:
<221> NAME/KEY: MISC_FEATURE
<222> LOCATION: (53)..(53)
<223> OTHER INFORMATION: Xaa at pos. 53 is Glu or Gly
<220> FEATURE:
<221> NAME/KEY: MISC_FEATURE
<222> LOCATION: (94)..(94)
<223> OTHER INFORMATION: Xaa at pos. 94 is Trp, Phe, or Gly

<400> SEQUENCE: 3

Asp Ile Gln Met Thr Gln Ser Pro Ser Ser Leu Ser Ala Ser Val Gly
1               5                   10                  15
Asp Arg Val Thr Ile Thr Cys Arg Ala Ser Xaa Ser Ile Gly Thr Arg
                20                  25                  30
```

```
Ile His Trp Tyr Gln Gln Lys Pro Gly Lys Ala Pro Lys Leu Leu Ile
            35                  40                  45

Tyr Phe Ala Ser Xaa Ser Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Lys Ile Xaa Pro Thr
                85                  90                  95

Thr Phe Gly Gly Gly Thr Lys Leu Glu Ile Lys
                100                 105
```

<210> SEQ ID NO 4
<211> LENGTH: 123
<212> TYPE: PRT
<213> ORGANISM: Artificial Sequence
<220> FEATURE:
<223> OTHER INFORMATION: Exemplified HCVR
<220> FEATURE:
<221> NAME/KEY: MISC_FEATURE
<222> LOCATION: (30)..(30)
<223> OTHER INFORMATION: Xaa at pos. 30 is Thr, Tyr, or Gly
<220> FEATURE:
<221> NAME/KEY: MISC_FEATURE
<222> LOCATION: (53)..(53)
<223> OTHER INFORMATION: Xaa at pos. 53 is Asn or Ser
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: MISC_FEATURE
<222> LOCATION: (101)..(101)
<223> OTHER INFORMATION: Xaa at pos. 101 is Ile or Val
<220> FEATURE:
<221> NAME/KEY: MISC_FEATURE
<222> LOCATION: (102)..(102)
<223> OTHER INFORMATION: Xaa at pos. 102 is Tyr or His

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Asp Tyr
                20                  25                  30

Asn Met His Trp Val Arg Gln Ala Pro Gly Gln Gly Leu Glu Trp Met
            35                  40                  45

Gly Tyr Ile Tyr Pro Tyr Xaa Gly Asp Thr Gly Tyr Asn Gln Asn Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Xaa Xaa Tyr Gly Tyr Leu Asn Val Ala Met Asp Ser
                100                 105                 110

Trp Gly Gln Gly Thr Leu Val Thr Val Ser Ser
            115                 120
```

<210> SEQ ID NO 5
<211> LENGTH: 11
<212> TYPE: PRT
<213> ORGANISM: Artificial Sequence
<220> FEATURE:
<223> OTHER INFORMATION: Exemplified LCDR1
<220> FEATURE:
<221> NAME/KEY: MISC_FEATURE

```
<222> LOCATION: (4)..(4)
<223> OTHER INFORMATION: Xaa at pos. 4 is Gln, Arg, or Glu

<400> SEQUENCE: 5

Arg Ala Ser Xaa Ser Ile Gly Thr Arg Ile His
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Exemplified LCDR2
<220> FEATURE:
<221> NAME/KEY: MISC_FEATURE
<222> LOCATION: (5)..(5)
<223> OTHER INFORMATION: Xaa at pos. 5 is Glu or Gly

<400> SEQUENCE: 6

Tyr Phe Ala Ser Xaa Ser Ile Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Exemplified LCDR3
<220> FEATURE:
<221> NAME/KEY: MISC_FEATURE
<222> LOCATION: (6)..(6)
<223> OTHER INFORMATION: Xaa at pos. 6 is Trp, Phe, or Gly

<400> SEQUENCE: 7

Gln Gln Ser Lys Ile Xaa Pro Thr Thr
1               5

<210> SEQ ID NO 8
<211> LENGTH: 13
<212> TYPE: PRT
<213> ORGANISM: Artificial Sequence
<220> FEATURE:
<223> OTHER INFORMATION: Exemplified HCDR1
<220> FEATURE:
<221> NAME/KEY: MISC_FEATURE
<222> LOCATION: (8)..(8)
<223> OTHER INFORMATION: Xaa at pos. 8 is Thr, Tyr, or Gly

<400> SEQUENCE: 8

Lys Ala Ser Gly Tyr Thr Phe Xaa Asp Tyr Asn Met His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Exemplified HCDR2
<220> FEATURE:
<221> NAME/KEY: MISC_FEATURE
<222> LOCATION: (6)..(6)
<223> OTHER INFORMATION: Xaa at pos. 6 is Asn or Ser

<400> SEQUENCE: 9

Tyr Ile Tyr Pro Tyr Xaa Gly Asp Thr Gly Tyr Asn Gln Asn Phe Lys
1               5                   10                  15
Ser
```

```
<210> SEQ ID NO 10
<211> LENGTH: 16
<212> TYPE: PRT
<213> ORGANISM: Artificial Sequence
<220> FEATURE:
<223> OTHER INFORMATION: Exemplified HCDR3
<220> FEATURE:
<221> NAME/KEY: MISC_FEATURE
<222> LOCATION: (5)..(5)
<223> OTHER INFORMATION: Xaa at pos. 5 is Ile or Val
<220> FEATURE:
<221> NAME/KEY: MISC_FEATURE
<222> LOCATION: (6)..(6)
<223> OTHER INFORMATION: Xaa at pos. 6 is Tyr or His

<400> SEQUENCE: 10

Ala Arg Gly Leu Xaa Xaa Tyr Gly Tyr Leu Asn Val Ala Met Asp Ser
1               5                   10                  15

<210> SEQ ID NO 11
<211> LENGTH: 642
<212> TYPE: DNA
<213> ORGANISM: Artificial Sequence
<220> FEATURE:
<223> OTHER INFORMATION: Nucleotide Sequence Encoding the Exemplified
      LC given by SEQ ID NO: 1
<220> FEATURE:
<221> NAME/KEY: misc_feature
<222> LOCATION: (79)..(79)
<223> OTHER INFORMATION: n at pos. 79 is c, a, or g
<220> FEATURE:
<221> NAME/KEY: misc_feature
<222> LOCATION: (80)..(80)
<223> OTHER INFORMATION: n at pos. 80 is a or g
<220> FEATURE:
<221> NAME/KEY: misc_feature
<222> LOCATION: (81)..(81)
<223> OTHER INFORMATION: n at pos. 81 is a or g
<220> FEATURE:
<221> NAME/KEY: misc_feature
<222> LOCATION: (158)..(158)
<223> OTHER INFORMATION: n at pos. 158 is a or g
<220> FEATURE:
<221> NAME/KEY: misc_feature
<222> LOCATION: (280)..(280)
<223> OTHER INFORMATION: n at pos. 280 is g or t
<220> FEATURE:
<221> NAME/KEY: misc_feature
<222> LOCATION: (281)..(281)
<223> OTHER INFORMATION: n at pos. 281 is g or t
<220> FEATURE:
<221> NAME/KEY: misc_feature
<222> LOCATION: (282)..(282)
<223> OTHER INFORMATION: n at pos. 282 is g or t

<400> SEQUENCE: 11
gacatccaga tgacccagtc tccatcctcc ctgtctgcat ctgtaggaga cagagtcacc      60
atcacttgca gggccagtnn nagcattggc acaagaatac actggtatca gcagaaacca     120
gggaaagccc ctaagctcct gatctatttt gcttctgngt ctatctctgg agtcccatca     180
aggttcagtg gcagtggatc tgggacagat tcactctca ccatcagcag cctgcagcct     240
gaagattttg caacttacta ctgtcaacaa agtaaaatcn nnccaacgac gttcggcgga     300
gggaccaagc tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
```

```
ctgagctcgc ccgtcacaaa gagcttcaac aggggagagt gc              642
```

<210> SEQ ID NO 12
<211> LENGTH: 1347
<212> TYPE: DNA
<213> ORGANISM: Artificial Sequence
<220> FEATURE:
<223> OTHER INFORMATION: Nucleotide Sequence Encoding the Exemplified
      HC given by SEQ ID NO: 2
<220> FEATURE:
<221> NAME/KEY: misc_feature
<222> LOCATION: (88)..(88)
<223> OTHER INFORMATION: n at pos. 88 is a, g, or t
<220> FEATURE:
<221> NAME/KEY: misc_feature
<222> LOCATION: (89)..(89)
<223> OTHER INFORMATION: n at pos. 89 is c, g, or a
<220> FEATURE:
<221> NAME/KEY: misc_feature
<222> LOCATION: (90)..(90)
<223> OTHER INFORMATION: n at pos. 90 is c, a, or t
<220> FEATURE:
<221> NAME/KEY: misc_feature
<222> LOCATION: (163)..(163)
<223> OTHER INFORMATION: n at pos. 163 is a or t
<220> FEATURE:
<221> NAME/KEY: misc_feature
<222> LOCATION: (164)..(164)
<223> OTHER INFORMATION: n at pos. 164 is a or c
<220> FEATURE:
<221> NAME/KEY: misc_feature
<222> LOCATION: (301)..(301)
<223> OTHER INFORMATION: n at pos. 301 is a or g
<220> FEATURE:
<221> NAME/KEY: misc_feature
<222> LOCATION: (303)..(303)
<223> OTHER INFORMATION: n at pos. 303 is c or t
<220> FEATURE:
<221> NAME/KEY: misc_feature
<222> LOCATION: (304)..(304)
<223> OTHER INFORMATION: n at pos. 304 is t or c
<220> FEATURE:
<221> NAME/KEY: misc_feature
<222> LOCATION: (306)..(306)
<223> OTHER INFORMATION: n at pos. 306 is c or t

<400> SEQUENCE: 12

```
caggtgcagc tggtgcagtc tggtgctgaa gtgaagaagc tggggcctc  agtgaaggtg   60 tcctgcaagg catctggata cacattcnnn gactacaaca tgcactgggt gcgacaggcc  120
cctggacaag gcttgagtg  gatgggatat atttatcctt acnntggtga tactgggtac  180
aaccagaatt tcaagagcag agtcaccatg accagggaca cgtccacgag cacagtctac  240
atggagctga gcagcctgag atctgaggac acggccgtgt attactgtgc gagaggatta  300
ntnnantacg gctaccttaa cgttgctatg gactcctggg gccaagggac actagtcaca  360
gtctcctcag cctccaccaa gggcccatcg gtcttcccgc tagcgccctg ctccaggagc  420
acctccgaga gcacagccgc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acgaagacct acacctgcaa cgtagatcac aagcccagca acaccaaggt ggacaagaga  660
gttgagtcca aatatggtcc cccatgccca ccctgcccag cacctgaggc cgccggggga  720
ccatcagtct tcctgttccc cccaaaaccc aaggacactc tcatgatctc ccggacccct  780
gaggtcacgt gcgtggtggt ggacgtgagc caggaagacc ccgaggtcca gttcaactgg  840
tacgtggatg gcgtggaggt gcataatgcc aagacaaagc cgcggaggga gcagttcaac  900
```

```
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag ggcagccccg agagccacag gtgtacaccc tgccccatc ccaggaggag    1080 atgaccaaga accaggtcag cctgacctgc ctggtcaaag gcttctaccc cagcgacatc   1140
gccgtggagt gggaaagcaa tgggcagccg gagaacaact acaagaccac gcctcccgtg   1200
ctggactccg acggctcctt cttcctctac agcaggctaa ccgtggacaa gagcaggtgg   1260
caggagggga atgtcttctc atgctccgtg atgcatgagg ctctgcacaa ccactacaca   1320
cagaagagcc tctccctgtc tctgggt                                        1347
```

```
<210> SEQ ID NO 13
<211> LENGTH: 11
<212> TYPE: PRT
<213> ORGANISM: Artificial
<220> FEATURE:
<223> OTHER INFORMATION: Exemplified LCDR1
<220> FEATURE:
<221> NAME/KEY: MISC_FEATURE
<222> LOCATION: (4)..(4)
<223> OTHER INFORMATION: Xaa at position 4 is an acyclic, polar amino
      acid with a charged entity

<400> SEQUENCE: 13

Arg Ala Ser Xaa Ser Ile Gly Thr Arg Ile His
1               5                   10

<210> SEQ ID NO 14
<211> LENGTH: 8
<212> TYPE: PRT
<213> ORGANISM: Artificial
<220> FEATURE:
<223> OTHER INFORMATION: Exemplified LCDR2
<220> FEATURE:
<221> NAME/KEY: MISC_FEATURE
<222> LOCATION: (5)..(5)
<223> OTHER INFORMATION: Xaa at position 5 is an acyclic amino acid

<400> SEQUENCE: 14

Tyr Phe Ala Ser Xaa Ser Ile Ser
1               5

<210> SEQ ID NO 15
<211> LENGTH: 9
<212> TYPE: PRT
<213> ORGANISM: Artificial
<220> FEATURE:
<223> OTHER INFORMATION: Exemplified LCDR3
<220> FEATURE:
<221> NAME/KEY: MISC_FEATURE
<222> LOCATION: (6)..(6)
<223> OTHER INFORMATION: Xaa at position 6 may be a neutral hydrophobic
      amino acid

<400> SEQUENCE: 15

Gln Gln Ser Lys Ile Xaa Pro Thr Thr
1               5

<210> SEQ ID NO 16
<211> LENGTH: 13
<212> TYPE: PRT
<213> ORGANISM: Artificial
<220> FEATURE:
<223> OTHER INFORMATION: Exemplified HCDR1
<220> FEATURE:
<221> NAME/KEY: MISC_FEATURE
<222> LOCATION: (8)..(8)
```

```
<223> OTHER INFORMATION: Xaa at position 8 may be a neutral polar or
      nonpolar amino acid

<400> SEQUENCE: 16

Lys Ala Ser Gly Tyr Thr Phe Xaa Asp Tyr Asn Met His
1               5                   10

<210> SEQ ID NO 17
<211> LENGTH: 17
<212> TYPE: PRT
<213> ORGANISM: Artificial
<220> FEATURE:
<223> OTHER INFORMATION: Exemplified HCDR2
<220> FEATURE:
<221> NAME/KEY: MISC_FEATURE
<222> LOCATION: (6)..(6)
<223> OTHER INFORMATION: Xaa at position 6 may be an acyclic, neutral,
      polar amino acid

<400> SEQUENCE: 17

Tyr Ile Tyr Pro Tyr Xaa Gly Asp Thr Gly Tyr Asn Gln Asn Phe Lys
1               5                   10                  15

Ser

<210> SEQ ID NO 18
<211> LENGTH: 16
<212> TYPE: PRT
<213> ORGANISM: Artificial
<220> FEATURE:
<223> OTHER INFORMATION: Exemplified HCDR3
<220> FEATURE:
<221> NAME/KEY: MISC_FEATURE
<222> LOCATION: (5)..(5)
<223> OTHER INFORMATION: Xaa at position 5 may be an acyclic,
      hydrophobic amino acid
<220> FEATURE:
<221> NAME/KEY: MISC_FEATURE
<222> LOCATION: (6)..(6)
<223> OTHER INFORMATION: Xaa at position 6 may be a cyclic, aromatic
      amino acid

<400> SEQUENCE: 18

Ala Arg Gly Leu Xaa Xaa Tyr Gly Tyr Leu Asn Val Ala Met Asp Ser
1               5                   10                  15
```